US00PP28425P3

(12) United States Plant Patent
Jensen

(10) Patent No.: US PP28,425 P3
(45) Date of Patent: Sep. 19, 2017

(54) ***TRIFOLIUM* PLANT NAMED 'TRIFPOT001'**

(50) Latin Name: *Trifolium repens*
Varietal Denomination: TRIFPOT001

(71) Applicant: Bent Juhl Jensen, Malling (DK)

(72) Inventor: Bent Juhl Jensen, Malling (DK)

( * ) Notice: Subject to any disclaimer, the term of this patent is extended or adjusted under 35 U.S.C. 154(b) by 133 days.

(21) Appl. No.: 14/756,663

(22) Filed: Sep. 29, 2015

(65) Prior Publication Data

US 2017/0094862 P1 Mar. 30, 2017

(51) Int. Cl.
*A01H 5/12* (2006.01)

(52) U.S. Cl.
USPC ..... Plt./373

(58) Field of Classification Search
USPC ..... Plt./263.1, 373
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Trifolium* plant named 'TRIFPOT001', characterized by its compact, upright to outwardly spreading and creeping plant habit; freely branching habit, dense and bushy appearance; dark brown to almost black-colored leaves with green-colored margins; numerous white-colored flowers blushed with pink arranged in dense capitula that are held above and beyond the foliar plane; and good garden performance.

3 Drawing Sheets

Botanical designation: *Trifolium repens*.
Cultivar denomination: 'TRIFPOT001'.

BACKGROUND OF THE INVENTION

The present invention relates to a new and distinct cultivar of *Trifolium* plant, botanically known as *Trifolium repens*, and hereinafter referred to by the name 'TRIFPOT001'.

The new *Trifolium* plant is a product of a planned breeding program conducted by the Inventor in Malling, Denmark. The objective of the breeding program is to create new compact and freely branching *Trifolium* plants with attractive foliage and inflorescences.

The new *Trifolium* plant originated from a cross-pollination in July, 2013 in Malling, Denmark of *Trifolium repens* 'Ebony', not patented, as the female, or seed, parent with a proprietary selection of *Trifolium repens* identified as code designation 09-001-001, not patented, as the male, or pollen, parent. The new *Trifolium* plant was discovered and selected by the Inventor as a flowering plant within the progeny of the stated cross-pollination in a controlled greenhouse environment in Malling, Denmark in March, 2014.

Asexual reproduction of the new *Trifolium* plant by vegetative cuttings in a controlled greenhouse environment in Malling, Denmark since June, 2014 has shown that the unique features of this new *Trifolium* plant are stable and reproduced true to type in successive generations.

SUMMARY OF THE INVENTION

Plants of the new *Trifolium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'TRIFPOT001'. These characteristics in combination distinguish 'TRIFPOT001' as a new and distinct *Trifolium* plant:

1. Compact, upright to outwardly spreading and creeping plant habit.
2. Freely branching habit, dense and bushy appearance.
3. Dark brown to almost black-colored leaves with green-colored margins.
4. Numerous white-colored flowers blushed with pink arranged in dense capitula that are held above and beyond the foliar plane.
5. Good garden performance.

Plants of the new *Trifolium* can be compared to plants of the female parent, 'Ebony'. Plants of the new *Trifolium* differ primarily from plants of 'Ebony' in the following characteristics:

1. Plants of the new *Trifolium* are more freely branching than plants of 'Ebony'.
2. Leaves of plants of the new *Trifolium* are darker brown in color than leaves of plants of 'Ebony'.
3. Plants of the new *Trifolium* and 'Ebony' differ in flower color as plants of 'Ebony' have pure white-colored flowers.

Plants of the new *Trifolium* can be compared to plants of the male parent selection. Plants of the new *Trifolium* differ primarily from plants of the male parent selection in the following characteristics:

1. Plants of the new *Trifolium* are more compact than and not as vigorous as plants of the male parent selection.
2. Plants of the new *Trifolium* are more freely branching than plants of the male parent selection.
3. Plants of the new *Trifolium* have shorter leaf petioles than plants of the male parent selection.
4. Plants of the new *Trifolium* and the male parent selection differ in flower color as plants of the male parent selection have pure white-colored flowers.

Plants of the new *Trifolium* can be compared to plants of the *Trifolium repens* 'Isabella', not patented. In side-by-side comparisons conducted in Malling, Denmark, plants of the new *Trifolium* differed from plants of 'Isabella' in the following characteristics:

1. Plants of the new *Trifolium* and 'Isabella' differed in leaf color as plants of 'Isabella' have red-colored leaves with green-colored centers.
2. Plants of the new *Trifolium* and 'Isabella' differed in flower color as plants of 'Isabella' have pure white-colored flowers.

BRIEF DESCRIPTION OF THE PHOTOGRAPHS

The accompanying colored photographs illustrate the overall appearance of the new *Trifolium* plant showing the colors as true as it is reasonably possible to obtain in colored reproductions of this type. Colors in the photographs may differ slightly from the color values cited in the detailed botanical description which accurately describe the colors of the new *Trifolium* plant.

The photograph on the first sheet is a side perspective view of a typical flowering plant of 'TRIFPOT001' grown in a container.

The photograph on the second sheet is a close-up view of the upper surface of a typical leaf of 'TRIFPOT001'.

The photograph on the third sheet is a close-up view of a typical inflorescence of 'TRIFPOT001'.

DETAILED BOTANICAL DESCRIPTION

The aforementioned photographs and following observations, measurements and values describe plants grown during the winter and early spring in 10.5-cm containers in a glass-covered greenhouse in Malling, Denmark and under cultural practices typical of commercial *Trifolium* production. During the production of the plants, day and night temperatures ranged from 16° C. to 18° C. Plants were 15 weeks old when the photographs and the description were taken. In the description, color references are made to The Royal Horticultural Society Colour Chart, 2007 Edition, except where general terms of ordinary dictionary significance are used.

Botanical classification: *Trifolium repens* 'TRIFPOT001'.

Parentage:

*Female, or seed, parent.*—*Trifolium repens* 'Ebony', not patented.

*Male or pollen parent.*—Proprietary selection of *Trifolium repens* identified as code number 09-001-001, not patented.

Propagation:

*Type.*—By vegetative cuttings.

*Time to initiate roots, summer and winter.*—About eight days at temperatures about 18° C.

*Time to produce a rooted young plant, summer and winter.*—About three weeks at temperatures about 18° C.

*Root description.*—Medium in thickness, fleshy; typically white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Container plant; compact, upright to outwardly spreading and creeping plant habit; moderately vigorous to vigorous growth habit.

*Branching habit.*—Freely branching habit typically with about 40 lateral branches developing per plant; dense and bushy appearance.

*Plant height.*—About 14.8 cm.

*Plant diameter* (*area of spread*).—About 36.8 cm.

Lateral branch description:

*Length.*—About 12.8 cm.

*Diameter.*—About 2 mm.

*Internode length.*—About 2.2 cm.

*Strength.*—Moderately strong to strong.

*Texture.*—Smooth, glabrous.

*Luster.*—Moderately glossy.

*Color.*—Close to 143B and 146A.

Leaf description:

*Arrangement.*—Leaves alternate and compound with three leaflets.

*Leaf length.*—About 3.4 cm.

*Leaf width.*—About 4.1 cm.

*Leaflet length.*—About 2.2 cm.

*Leaflet width.*—About 1.7 cm.

*Leaf shape.*—Orbicular in outline.

*Leaflet shape.*—Ovate.

*Leaflet apex.*—Broadly acute to obtuse.

*Leaflet base.*—Obtuse.

*Leaflet margin.*—Finely serrate.

*Texture, upper and lower surfaces.*—Smooth, glabrous.

*Luster, upper surface.*—Matte.

*Luster, lower surface.*—Slightly glossy.

*Venation pattern.*—Pinnate.

*Color.*—Developing leaves, upper surface: Close to 200A to 200B; margins, close to 138B. Developing leaves, lower surface: Close to 200A; margins, close to 138B. Fully expanded leaves, upper surface: Close to between 200A and 203B; margins, close to 138B; venation, close to 138A to 138B. Fully expanded leaves, lower surface: Close to 200A; margins, close to 138B; venation, close to 146A.

*Petioles.*—Length: About 13.6 cm. Diameter: About 1.5 mm. Texture, upper and lower surfaces: Smooth, glabrous. Color, upper and lower surfaces: Close to 143A.

Flower description:

*Flower arrangement and flowering habit.*—Small papilionaceous flowers arranged in dense capitula that are held above and beyond the foliar plane; continuous and freely flowering habit with about 55 flowers developing per capitulum and about 4,400 flowers developing per plant; flowers face mostly outwardly.

*Fragrance.*—Faintly fragrant, sweet and pleasant.

*Natural flowering season.*—Plants flower in the garden from the spring until the autumn.

*Flower longevity.*—Flowers maintain good substance for about one week on the plant; flowers not persistent.

*Inflorescence diameter.*—About 2.1 cm.

*Inflorescence height.*—About 2.6 cm.

*Flower diameter.*—About 4 mm by 5 mm.

*Flower length* (*height*).—About 8 mm.

*Flower buds.*—Length: About 7 mm. Diameter: About 2 mm. Shape: Oblanceolate. Color: Calyx, close to 145C and 138A; developing petals, close to NN155D tinged with close to 75D.

*Petals.*—Arrangement: Five petals in a single whorl; one banner or vexillum petal, two wing or lateral petals and two lower petals fused to form a sheath or keel enclosing the reproductive organs; petals fused toward the base. Length, banner petal: About 9 mm. Length, lateral petals: About 7 mm. Length, lower petals: About 6 mm. Width, banner petal: About 4 mm. Width, lateral petals: About 1.5 mm. Width, lower petals: About 0.5 mm. Shape, banner petal: Obovate. Shape, lateral petals: Elliptical. Shape, lower petals: Ovate. Apex, banner and lower petals: Shallowly retuse. Apex, lateral petals: Acute. Base, all petals: Fused. Margin, all petals: Entire. Texture, all petals, upper and lower surfaces: Smooth, glabrous. Luster, all petals, upper and lower surface: Matte. Color, banner petal: When opening, upper surface: Close to NN155D tinged with close to 75C. When opening, lower surface: Close to NN155D; towards the base, tinged with close to 145D. Fully opened, upper and lower surfaces: Close to NN155D slightly tinged with close to 75D; color does not change with development. Color, lateral petals: When opening, upper and lower surfaces: Close to NN155C. Fully opened, upper and lower surfaces: Close to NN155C. Color, lower petals: When opening, upper and lower surfaces: Close to 150D. Fully opened, upper and lower surfaces: Close to 150D.

*Sepals*.—Appearance: Five sepals fused into a campanulate-shaped calyx. Length: About 5 mm. Width: About 0.75 mm. Shape: Lanceolate. Apex: Narrowly acute. Margin: Entire. Texture, upper and lower surfaces: Smooth, glabrous. Luster, upper and lower surfaces: Matte. Color: When opening, upper and lower surfaces: Fused portion, close to 145C; free portion, close to 138A. Fully opened, upper and lower surfaces: Fused portion, close to 145C; free portion, close to 138A.

*Peduncles*.—Length: About 14.2 cm. Diameter: About 2 mm. Strength: Moderately strong. Aspect: About 40° from lateral branch. Texture: Smooth, glabrous. Color: Close to 143B.

*Pedicels*.—Length: About 4 mm. Diameter: About 0.5 mm. Strength: Moderately strong. Aspect: About 80° from vertical. Texture: Smooth, glabrous. Color: Close to 145A.

*Reproductive organs*.—Androecium: Stamen number: About eight per flower. Filament length: About 5 mm. Filament color: Close to 157D; towards the base, close to 155C. Anther shape: Flattened orbicular; basifixed. Anther length: About 0.02 mm. Anther color: Close to 11A. Amount of pollen: Moderate. Pollen color: Close to 11C. Gynoecium: Pistil length: About 3 mm. Style length: About 2.75 cm. Style texture: Smooth, glabrous. Style color: Close to 145D. Stigma appearance: Club-shaped. Stigma color: Close to 144A. Ovary color: Close to 144B.

*Seeds and fruits*.—Seed and fruit development have not been observed on plants of the new *Trifolium*.

Garden performance: Plants of the new *Trifolium* have been observed to have good garden performance and to tolerate wind, rain and high temperatures about 40° C.; plants of the new *Trifolium* are winter-hardy and are hardy to USDA Hardiness Zone 4.

Pathogen & pest resistance: Plants of the new *Trifolium* have not been observed to be resistant to pathogens and pests common to *Trifolium* plants.

It is claimed:

1. A new and distinct *Trifolium* plant named 'TRIFPOT001' as illustrated and described.

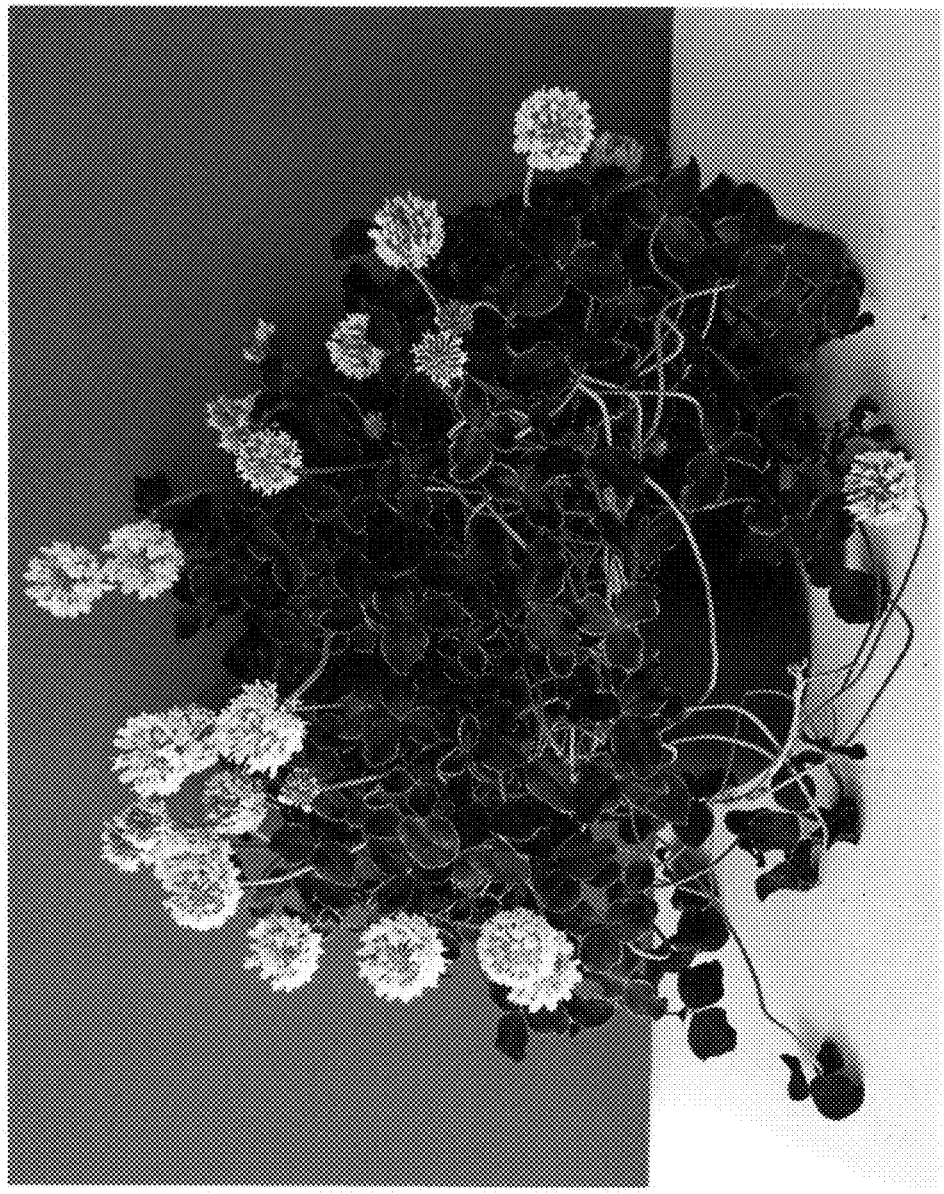

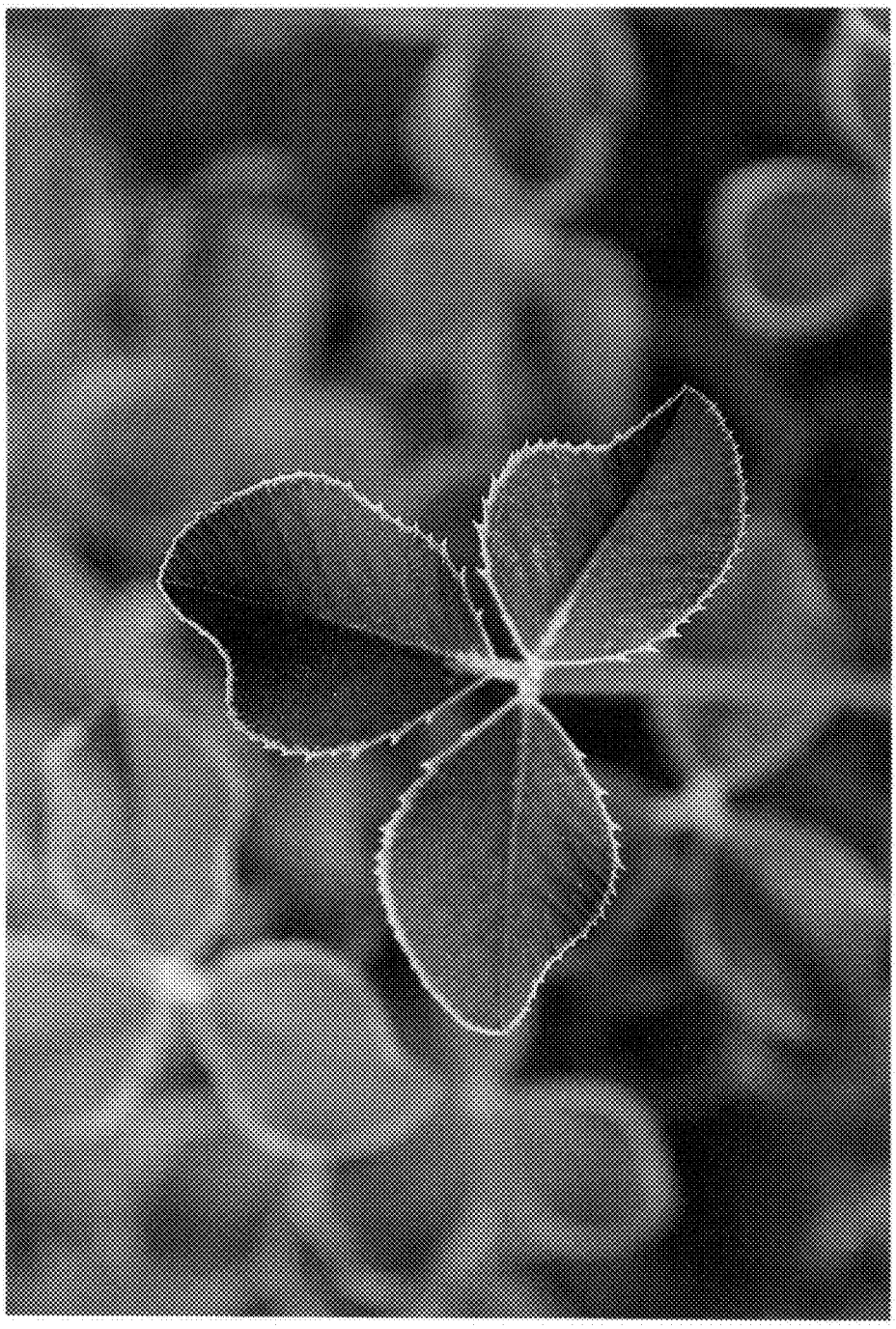

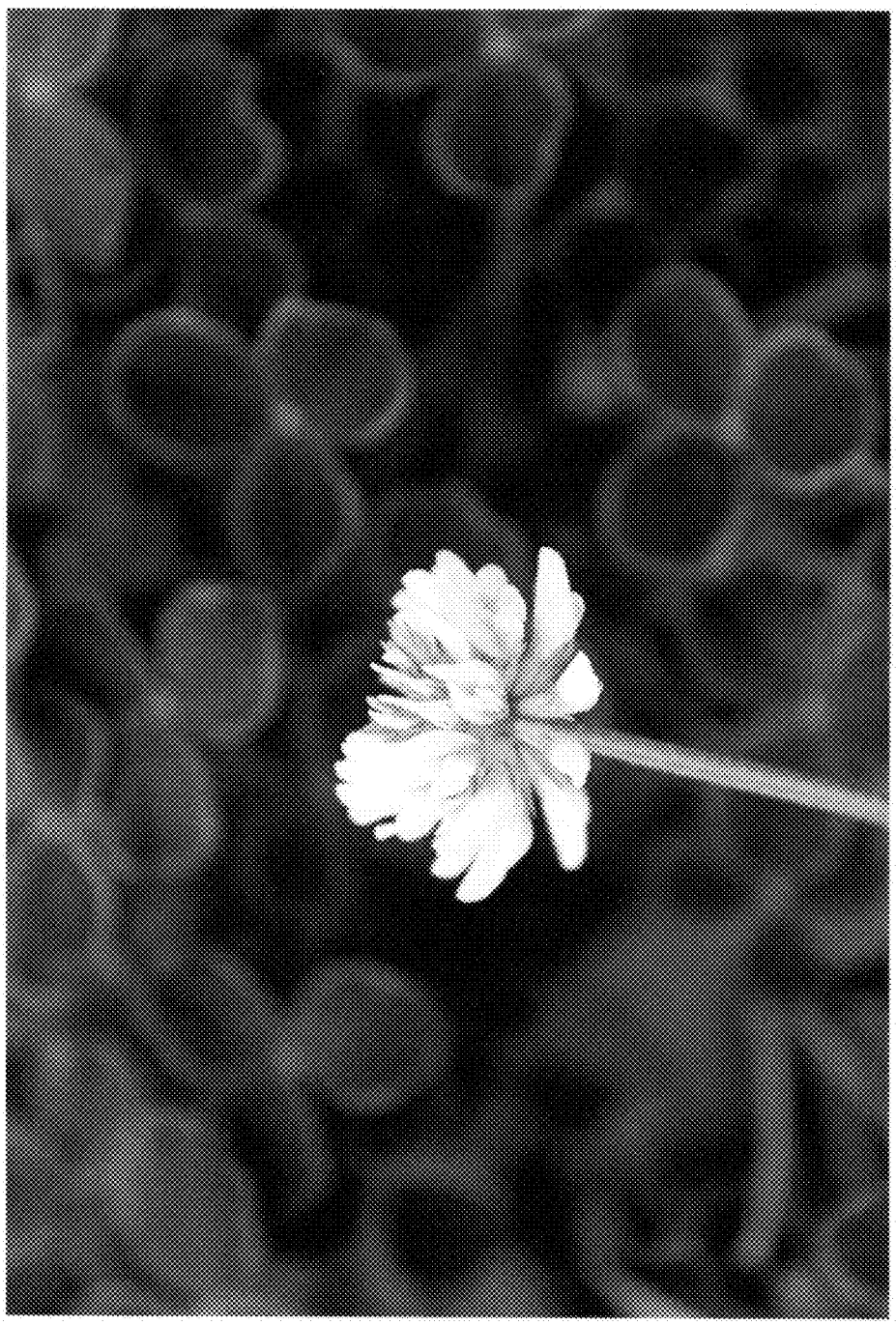

* * * * *